(12) United States Patent
Nelson et al.

(10) Patent No.: US 7,836,767 B2
(45) Date of Patent: *Nov. 23, 2010

(54) MECHANISM FOR ADAPTIVE CONTOUR COMPLIANCE

(75) Inventors: W. Robert Nelson, Wichita, KS (US); C. Tim Harbaugh, Derby, KS (US)

(73) Assignee: Spirit AeroSystems, Inc., Wichita, KS (US)

( * ) Notice: Subject to any disclaimer, the term of this patent is extended or adjusted under 35 U.S.C. 154(b) by 7 days.

This patent is subject to a terminal disclaimer.

(21) Appl. No.: 12/398,639

(22) Filed: Mar. 5, 2009

(65) Prior Publication Data

US 2009/0165562 A1 Jul. 2, 2009

Related U.S. Application Data

(63) Continuation of application No. 11/865,554, filed on Oct. 1, 2007, now Pat. No. 7,637,162.

(51) Int. Cl.
*G01N 29/26* (2006.01)
(52) U.S. Cl. ............... 73/618; 73/583; 73/635; 73/640; 73/641
(58) Field of Classification Search ............... 73/618, 73/583, 634, 635, 640, 641, 1.79, 1.81, 588, 73/598, 600, 865.8
See application file for complete search history.

(56) References Cited

U.S. PATENT DOCUMENTS

| | | | | |
|---|---|---|---|---|
| 3,678,736 A * | 7/1972 | May | ............... | 73/634 |
| 3,771,354 A * | 11/1973 | Miller | ............... | 73/639 |
| 3,913,388 A * | 10/1975 | Berner et al. | ............... | 73/634 |
| 4,065,976 A * | 1/1978 | Taenzer et al. | ............... | 73/633 |
| 4,100,809 A * | 7/1978 | Bobrov et al. | ............... | 73/638 |
| 4,117,733 A * | 10/1978 | Gugel | ............... | 73/634 |
| 4,258,319 A * | 3/1981 | Shimada et al. | ............... | 324/226 |
| 4,312,230 A * | 1/1982 | Bricker et al. | ............... | 73/638 |
| 4,375,167 A * | 3/1983 | Nusbickel et al. | ............... | 73/644 |
| 4,398,421 A * | 8/1983 | White | ............... | 73/597 |
| 5,064,340 A * | 11/1991 | Genov et al. | ............... | 414/744.5 |
| 6,637,266 B1 * | 10/2003 | Froom | ............... | 73/583 |
| 7,637,162 B2 * | 12/2009 | Nelson et al. | ............... | 73/618 |

* cited by examiner

*Primary Examiner*—J M Saint Surin
(74) *Attorney, Agent, or Firm*—Hovey Williams LLP

(57) ABSTRACT

An apparatus for inspecting samples that may include a curvature that varies from sample to sample comprises a scanning element, a feed mechanism, and a pivot mechanism. The scanning element transmits and receives a signal to and from the sample as the sample passes by, thereby building an image or profile of the sample. The feed mechanism includes a drive motor coupled to a series of pulleys and belts that form an open-ended chain. The pulleys rotate when driven by the drive motor and are coupled to an array of rollers that rotate as well to propel a inspection sample past the scanning element. The pivot mechanism includes a series of primary and secondary links that also form an open-ended chain. The primary links are coupled to the rollers and the combination pivots in unison to form an arc that matches the curvature of the sample in order to maintain a fixed distance between the sample and the scanning element.

17 Claims, 13 Drawing Sheets

MECHANISM FOR ADAPTIVE CONTOUR COMPLIANCE

RELATED APPLICATIONS

The present application is continuation patent application and claims priority benefit, with regard to all common subject matter, of earlier-filed U.S. nonprovisional patent application titled "MECHANISM FOR ADAPTIVE CONTOUR COMPLIANCE," Ser. No. 11/865,554, filed Oct. 1, 2007. The identified earlier-filed application is hereby incorporated by reference into the present application.

BACKGROUND OF THE INVENTION

1. Field of the Invention

Embodiments of the present invention relate to non-destructive inspection. More particularly, embodiments of the present invention relate to non-destructive inspection using a scanning element mounted to an adaptive contour compliance apparatus to test samples that may include a curvature that varies from sample to sample.

2. Description of the Related Art

Non-destructive inspection involves the examination of parts, often in a production environment, wherein some characteristic of the part is measured to evaluate a certain aspect of the part, such as the quality of construction. As opposed to other techniques to gauge the quality of a part or to find defects, such as cross sectioning, drilling or excising a portion of the part, all of which may destroy the part or at least render the part unusable, non-destructive inspection does not typically harm the part in any way. Often, the methods of non-destructive inspection include scanning a part by transmitting a form of radiation at the part and recording the reflected or perhaps refracted radiation to form an image or profile of the part. Sorting or rejection of parts may take place based on the image or profile of the part.

Non-destructive inspection mechanisms typically either manipulate the part in order to scan it or move the inspection element along the surface of the part in order to make a scan. Mobile inspection mechanisms can often scan parts that may include a curvature, although the mechanisms may be unsuitable or inefficient for scanning elongated parts that have a small cross-sectional area such as a shear tie. Stationary inspection mechanisms are often well-suited for scanning elongated parts that have a small cross-sectional area. However, these stations may not be able to handle samples that have a curvature or the stations may be set up to handle only a fixed radius of curvature. Thus, there is a need for a stationary inspection mechanism that can inspect samples that may have a curvature which varies from sample to sample.

SUMMARY OF THE INVENTION

Embodiments of the present invention solve the above-mentioned problems and provide a distinct advance in the art of non-destructive inspection. More particularly, embodiments of the invention provide non-destructive inspection using a scanning element on samples that may be elongated with a small cross-sectional area and include a curvature that varies from sample to sample. In addition, the sample to be inspected typically includes a protruding feature such as a flange or lip.

In various embodiments, the present invention is an apparatus for inspecting samples that may include a curvature that varies from sample to sample. The apparatus includes a scanning element, a feed mechanism, and a pivot mechanism. The scanning element typically transmits and receives a signal to and from the sample as the sample passes by, thereby building an image or profile of the sample. The scanning element is located in the center of the feed and pivot mechanisms.

The feed mechanism, responsible for guiding the sample past the scanning element, is actuated by a drive motor, which is coupled to a series of pulleys by a series of belts to form an open-ended chain, wherein each belt provides a link between two pulleys. Thus, the drive motor can drive the series of pulleys to rotate generally synchronously and in the same direction.

The feed mechanism also includes a plurality of shafts, gears, and rollers that form two arrays—a rear array and a front array. Each element of the rear array is identical to each element of the front array and includes a shaft rigidly attached to a gear and a roller. In addition, the rear shafts are coupled to the front shafts by a plurality of swing arms such that the rear shafts and rollers are generally aligned with the front shafts and rollers to form pairs of shafts and rollers. And, the rear gears contact the front gears such that rotation of the rear shafts and rollers in one direction causes rotation of the front shafts and rollers in the opposite direction. Furthermore, the rear shafts are coupled to the pulleys. Therefore, the drive motor drives the series of pulleys and all of the rear array elements to rotate generally synchronously and in one direction, while all of the front array elements are driven to rotate generally synchronously and in the opposite direction.

The feed mechanism generally allows the front array of rollers to contact one side of the sample while the rear array of rollers contacts the other side of the sample. The swing arms also allow the front shafts and rollers to swing about the rear shafts and rollers. The feed mechanism includes a plurality of springs coupled to pivot mechanism that force the front rollers to swing about the rear rollers. With the force of the springs on the front rollers, this structure allows the front rollers to press the sample against the rear rollers, thus helping to propel the sample as the rollers rotate and guide the sample past the scanning element. The feed mechanism also includes a plurality of stoppers that limit the swing angle of the front rollers about the rear rollers in order to allow the sample to pass through the rollers.

The pivot mechanism, which adapts the feed mechanism to the curvature of the sample in order to maintain a constant distance between the scanning element and the sample, comprises a plurality of primary links and secondary links. Each primary link includes a head portion and a tail portion, wherein the plurality of primary links are joined together to form an open-ended chain, with the tail of one primary link coupled to the head of the next primary link. At the point where the primary links are coupled together, each primary link can pivot. In addition, at each pivot point the primary links are coupled with the rear array of shafts. Thus, as the primary links pivot in relation to one another, the rear array of shafts and rollers and (by extension through the swing arms) the front array of shafts and rollers move in relation to one another. Furthermore, a plurality of secondary links couple the tail of one primary link to the head of the primary link that is two links away in order to force all the primary links to pivot generally in unison. Therefore, the arrays of shafts and rollers move in relation to one another generally in unison as well. As a result, with this structure, the feed mechanism, as governed by the pivot mechanism, always maintains the shape of a straight line or an arc of varying radius of curvature, which allows the feed mechanism to adapt to the curvature of the sample.

The apparatus operates by powering the drive motor to rotate the pulleys and thereby, the rear array of shafts and rollers. The front array of shafts and rollers rotates in the opposite direction as the rear array. A sample to be inspected is inserted at one end of the feed mechanism between the front array of rollers and the rear array of rollers so that the rollers contact the protruding feature of the sample. Pressure from the springs helps to squeeze each pair of rollers against the sample to propel the sample from one pair of rollers in the array to the next. A discontinuity, or gap, may exist in the test sample along the edge where the rollers grip the sample, however rollers ahead of and behind the discontinuity maintain uninterrupted forward motion of the sample through the feed mechanism.

As the sample progresses forward through each pair of rollers, the primary links in the pivot mechanism pivot to adjust to the curvature of the sample. As the sample passes through the third pair of rollers, the shape of the feed mechanism, as controlled by the pivot mechanism, is set to match the radius of curvature of the sample. The scanning element is located in the center of the array of rollers and scans the sample by transmitting a signal to the sample and receiving a signal back as the sample passes by on its journey through the feed mechanism. The sample continues through the feed mechanism and is expelled after it passes through the last pair of rollers.

This summary is provided to introduce a selection of concepts in a simplified form that are further described below in the detailed description. This summary is not intended to identify key features or essential features of the claimed subject matter, nor is it intended to be used to limit the scope of the claimed subject matter.

Other aspects and advantages of the present invention will be apparent from the following detailed description of the preferred embodiments and the accompanying drawing figures.

BRIEF DESCRIPTION OF THE DRAWING FIGURES

A preferred embodiment of the present invention is described in detail below with reference to the attached drawing figures, wherein.

Figure 1:
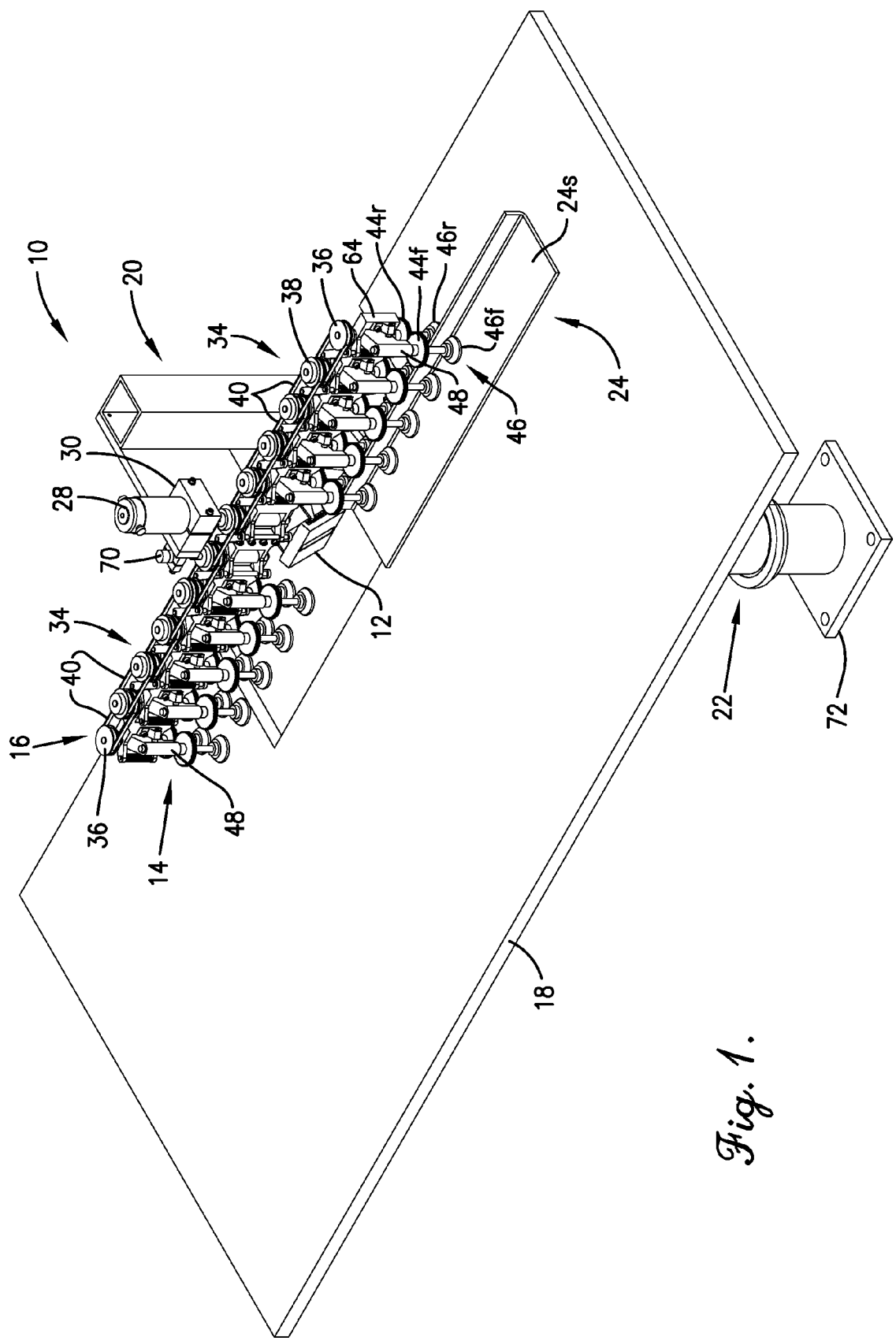
FIG. 1 is a perspective view of an adaptive contour compliance apparatus, constructed in accordance with an embodiment of the invention, that is scanning a straight test sample.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE PREFERRED EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

FIG. 1 shows an adaptive contour compliance apparatus 10 constructed in accordance with an embodiment of the invention. The apparatus 10 includes a scanning element 12, a feed mechanism 14, a pivot mechanism 16, a table 18, a frame 20, and a base 22. The apparatus 10 is operable to scan a test sample 24. The test sample 24 may be straight 24s, as shown in FIG. 1-FIG. 6, or may be curved 24c, as shown in FIG. 9-FIG. 12. Test samples 24 may include aircraft fuselage components such as stringers and shear ties. However, generally, the apparatus 10 is operable to test any sample of similar cross section that may be gripped by the feed mechanism 14 and is of sufficient length to be adapted to by the pivot mechanism 16.

As shown in FIG. 1, the apparatus 10 is about to scan a test sample 24 that has just entered the feed mechanism 14. Thus, the entry point for a test sample 24 into the apparatus 10 is to the right end of the feed mechanism 14 when facing the scanning element 12 of the apparatus 10. Furthermore, the forward direction of the test sample 24 is from right to left through the feed mechanism 14 when facing the scanning element 12.

The scanning element 12 generally scans a test sample 24 to create an image or a profile of the sample 24 for quality control purposes that sorts good parts from bad, or perhaps to characterize a manufacturing or assembly process. Typically, the scanning element 12 transmits a signal to the test sample 24 and senses the reflected signal from the sample 24. In some embodiments, the scanning element 12 includes an ultrasonic scanner that sends and receives an ultrasonic signal to the sample 24. In other embodiments, the scanning element 12 may include an infrared scanner or x-ray scanner.

Generally, the scanning element 12 is connected to a general-purpose data processing element, such as a computer, or electronics testing equipment, or combinations thereof. The data processing element or test equipment typically generates test signals and stores received test data and may be in communication with other manufacturing or assembly equipment.

The scanning element 12 may also include a scanner positioning element 26. In various embodiments, the scanner positioning element 26 may include manual adjust components such as positioning arms coupled together with easy-to-adjust fasteners such as wing nuts. In other embodiments, the scanner positioning element 26 may include automatically adjusted components, such as computer-controlled motorized positioners.

The feed mechanism 14 generally guides the test sample 24 past the scanning element 12. In various embodiments, the feed mechanism 14 is actuated by a drive motor 28. Other types of actuators are possible that produce a rotating output. The drive motor 28 is coupled to a drive motor housing 30 that is attached to the frame 20. The drive motor housing 30 may include a gearing mechanism to modify the performance of the drive motor 28, such as to increase torque. The drive motor housing 30 may also include a drive shaft 32, such that rotation of the drive motor 28 generally causes rotation of the drive shaft 32.

Figure 2:
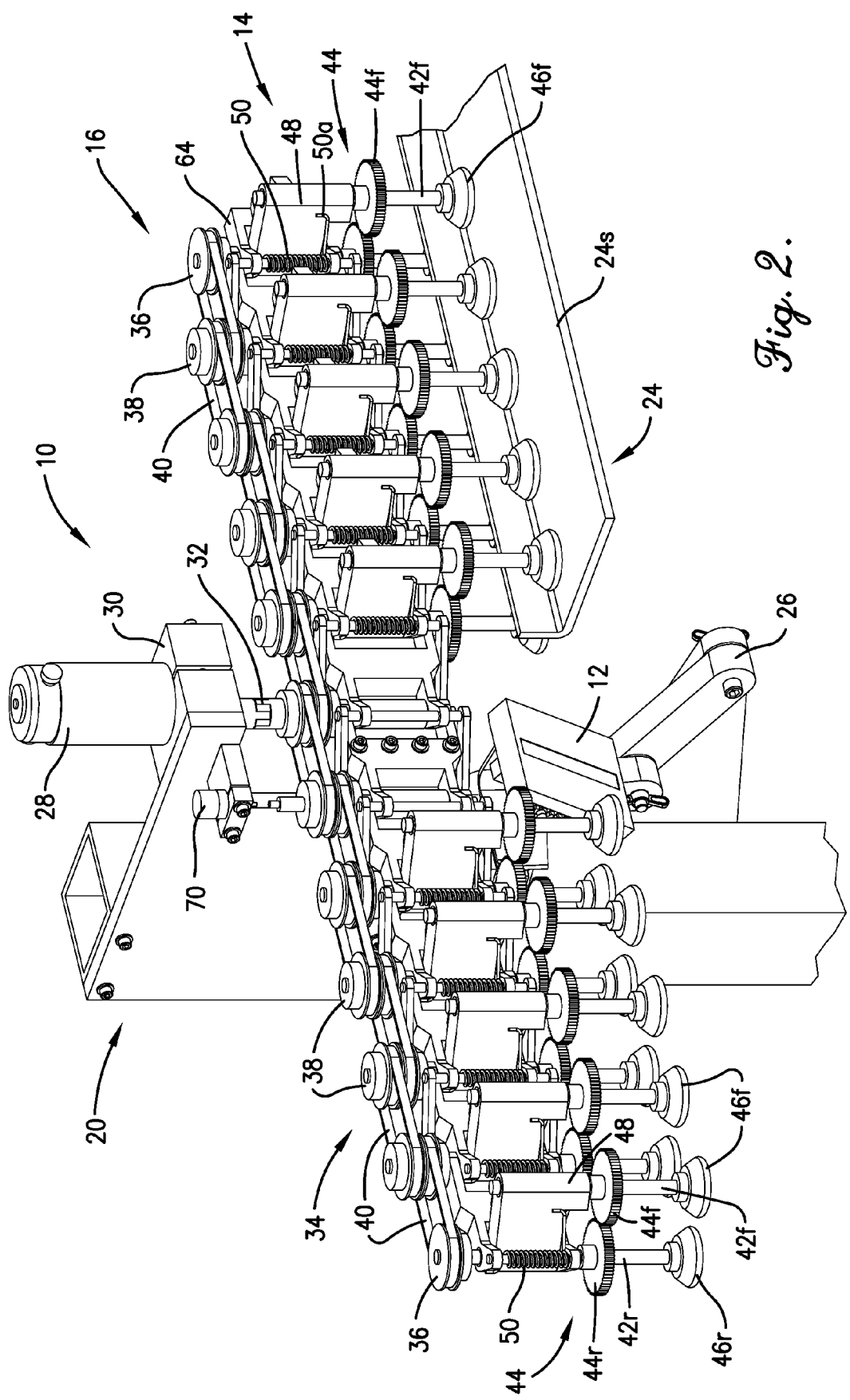
FIG. 2 is a perspective view of the apparatus, showing greater detail.
Figure 3:
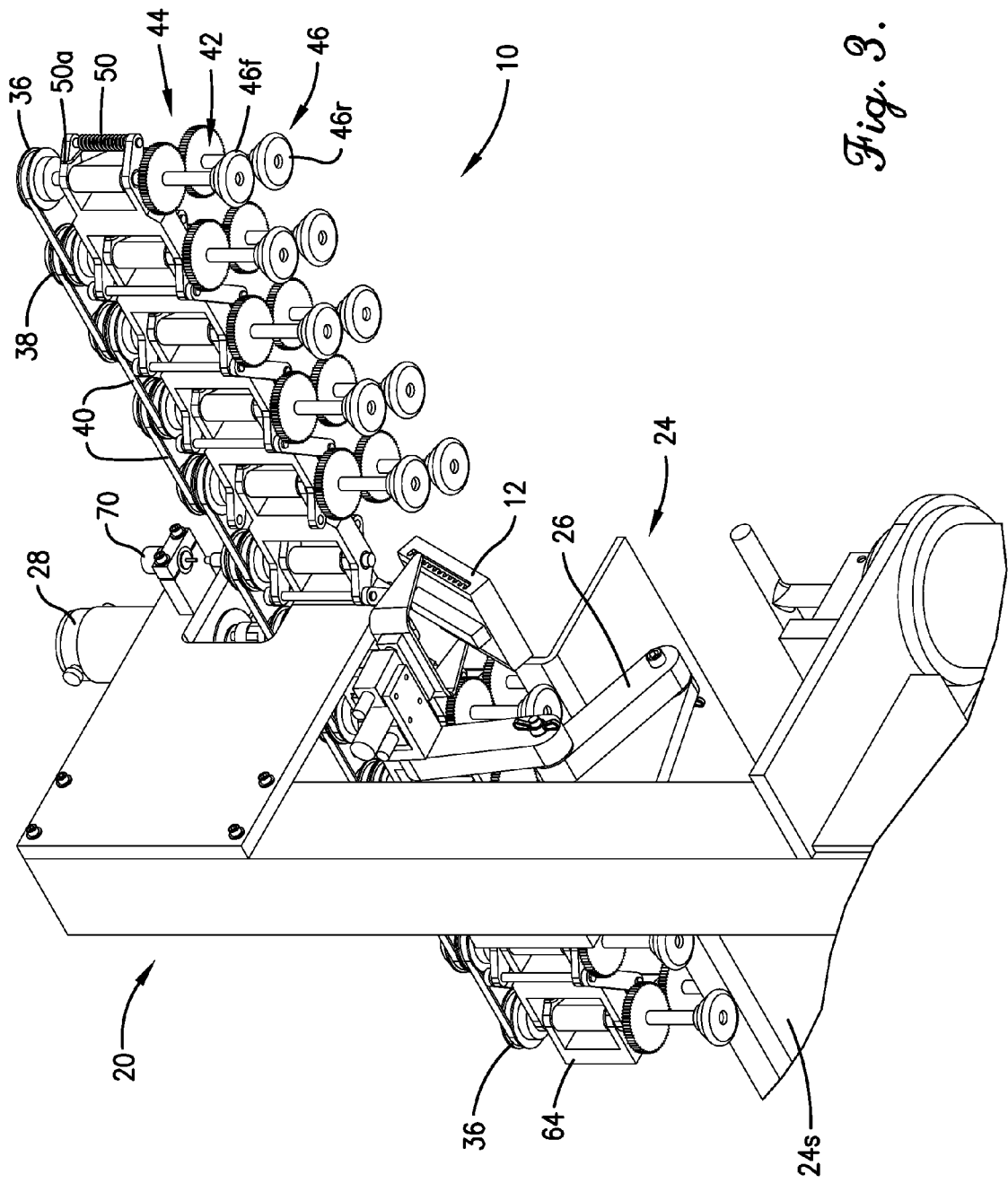
FIG. 3 is a perspective view of the apparatus as seen from underneath and slightly behind the apparatus.
Figure 4:
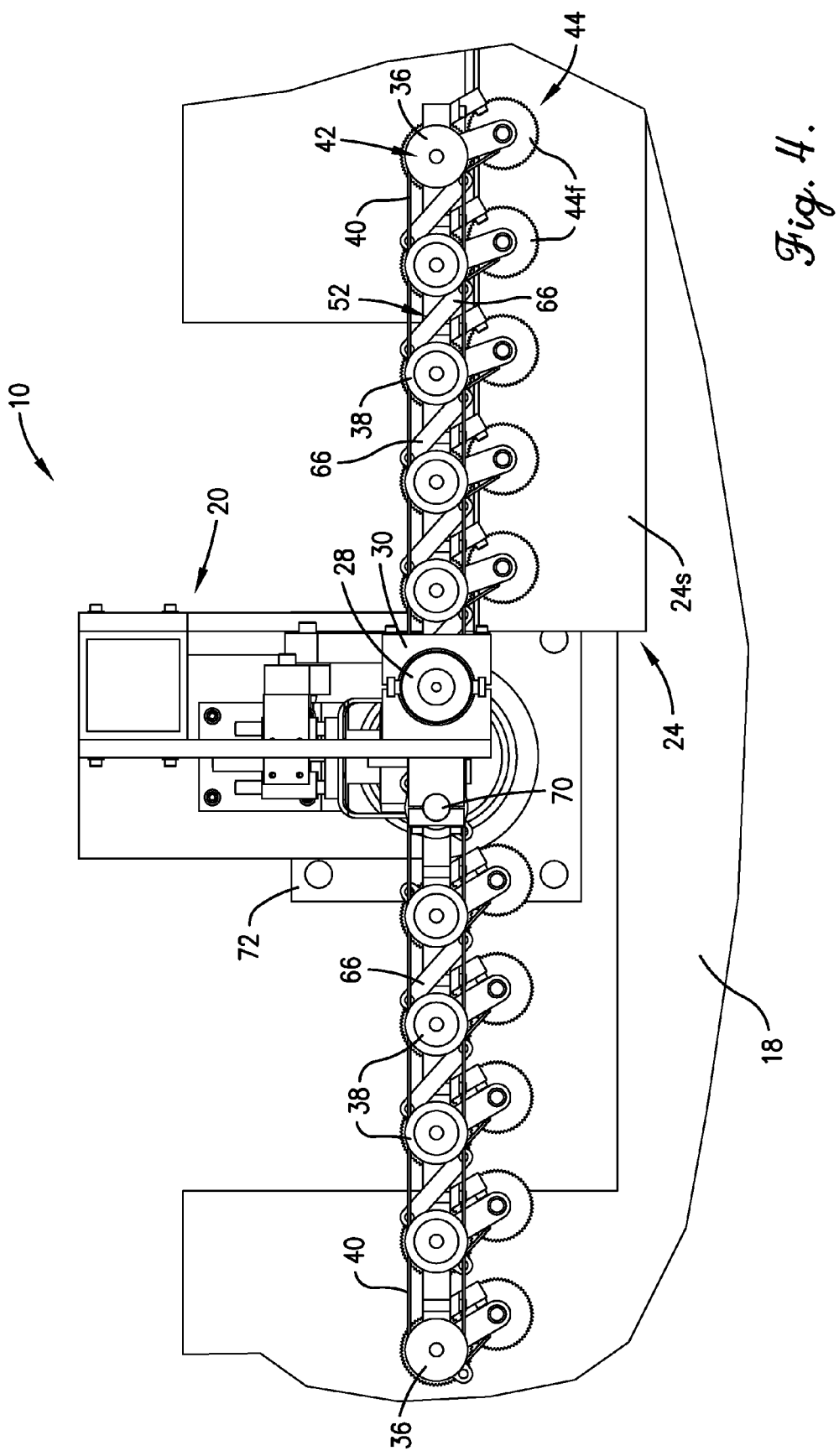
FIG. 4 is a top plan view of the apparatus.
Figure 5:
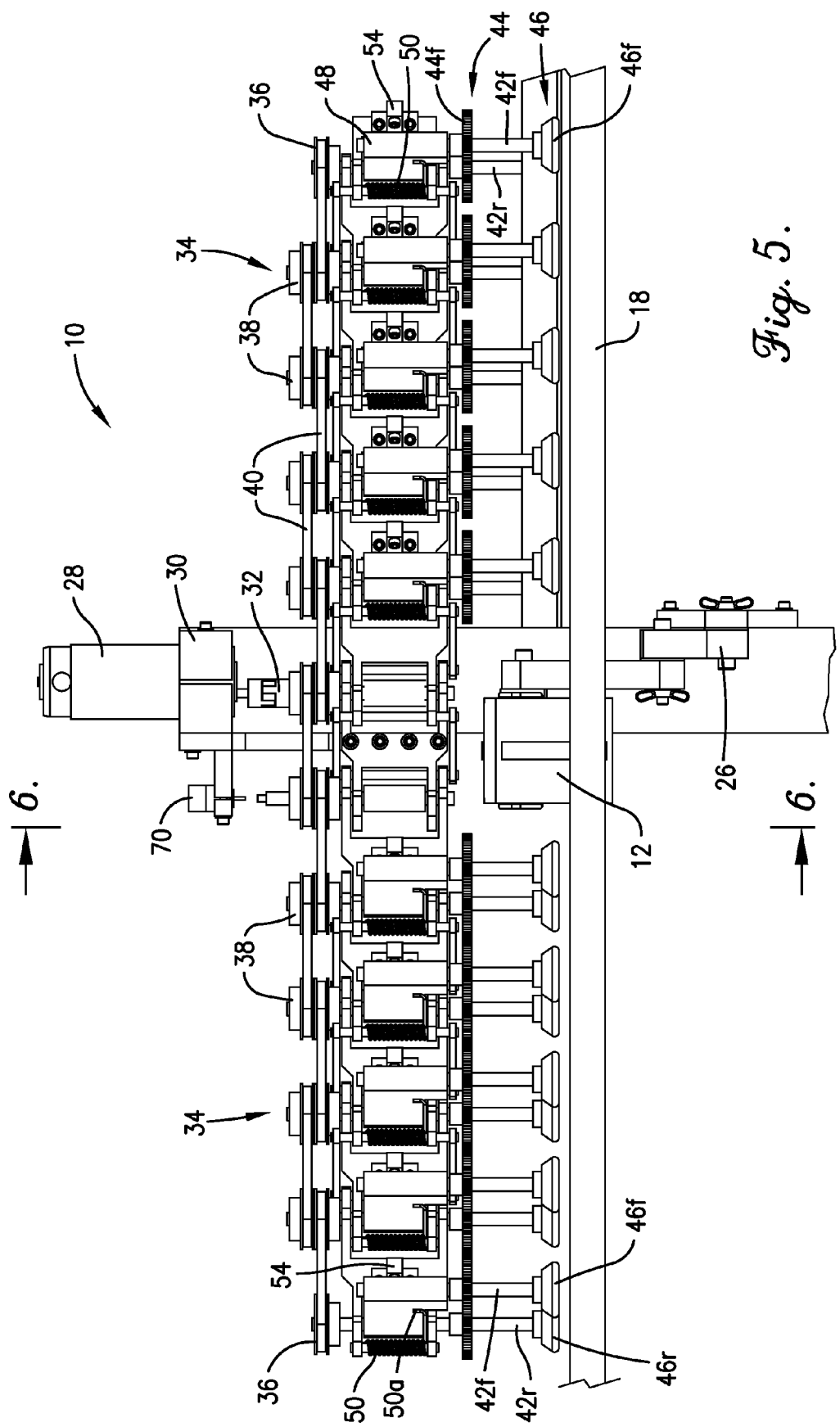
FIG. 5 is a front plan view of the apparatus.

In various embodiments, the apparatus 10 includes a plurality of pulleys 34, as seen in FIG. 2, which may include single-level pulleys 36 and double-level pulleys 38. The drive shaft 32 is coupled to one of the pulleys 34, typically a pulley 34 that does not pivot with the pivot mechanism 16 (discussed in greater detail below), which is generally a double-level pulley 38.

The apparatus 10 also includes a plurality of belts 40 that couple to the pulleys 34. The belts 40 are typically flexible and manufactured from a form of rubber. The single-level pulleys 36 are generally located at opposing ends of the feed mechanism 14 and couple to one belt 40. The double-level pulleys 38 are located in the middle of the feed mechanism 14 and couple to two belts 40. Given this structure, the belts 40 in combination with the pulleys 34 generally form an open-ended chain, with each belt 40 linking two pulleys 34 together.

Since the pulleys 34 are coupled together by the belts 40, all the pulleys 34 are operable to rotate generally synchronously and in the same direction. Furthermore, because the drive shaft 32 is coupled to one of the pulleys 34, all of the pulleys 34 are operable to be driven by the drive motor 28 such that rotation of the drive motor 28 through the drive shaft 32 generally causes rotation of all of the pulleys 34 generally synchronously and in the same direction.

Figure 7:
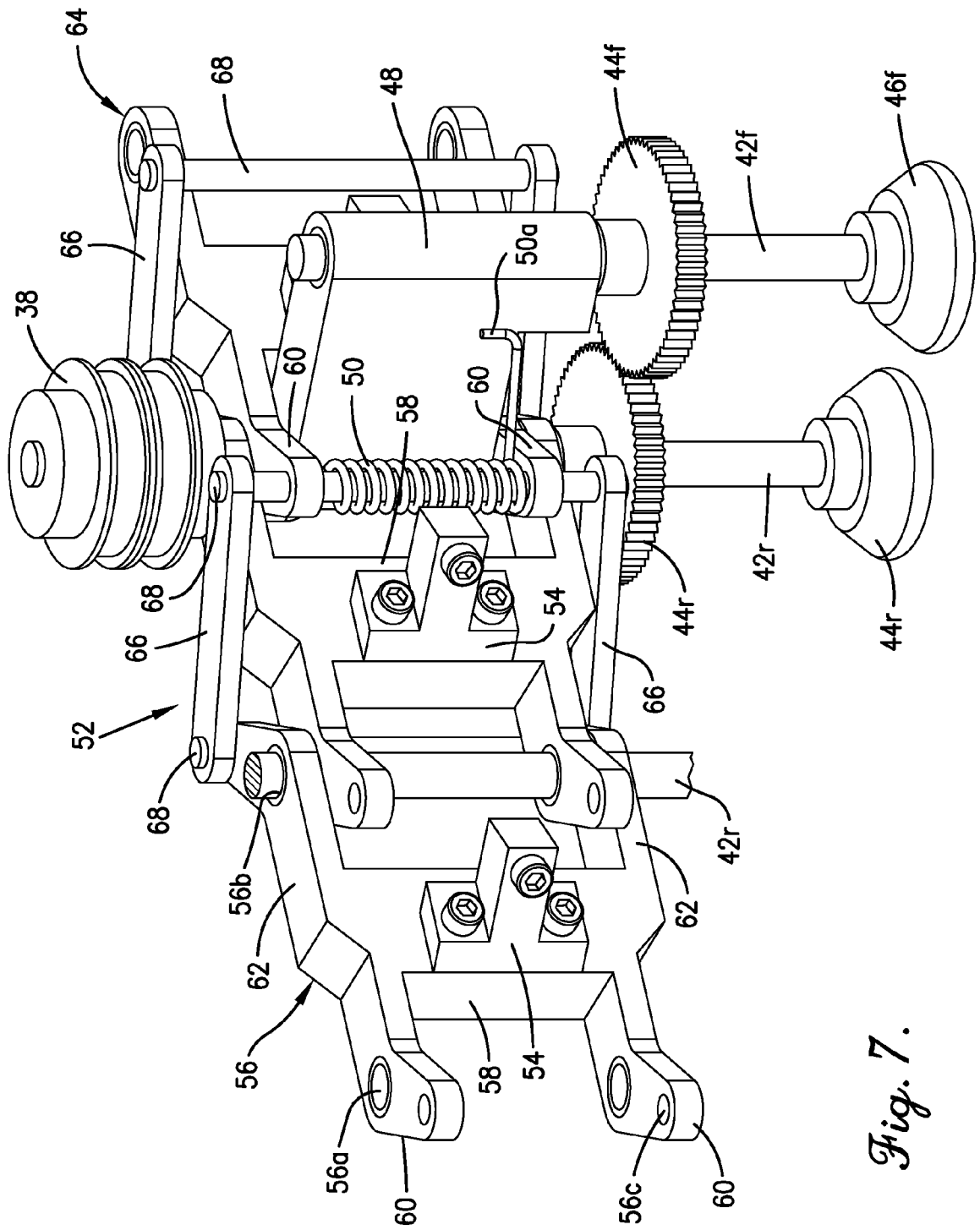
FIG. 7 is an isolated view of a portion of the feed mechanism and pivot mechanism as seen from one side.
Figure 8:
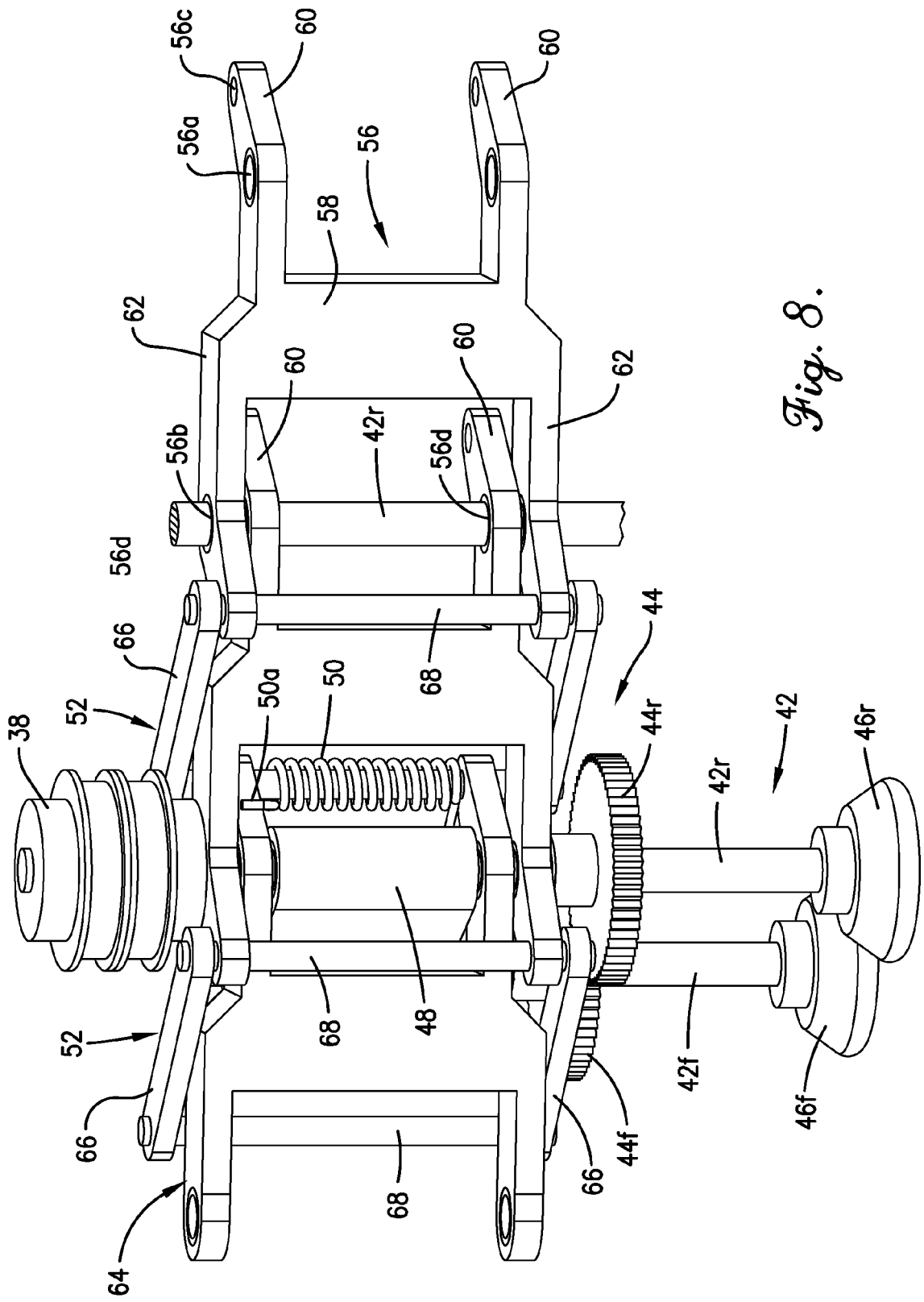
FIG. 8 is an isolated view of a portion of the feed mechanism and pivot mechanism as seen from a rear perspective view.
Figure 9:
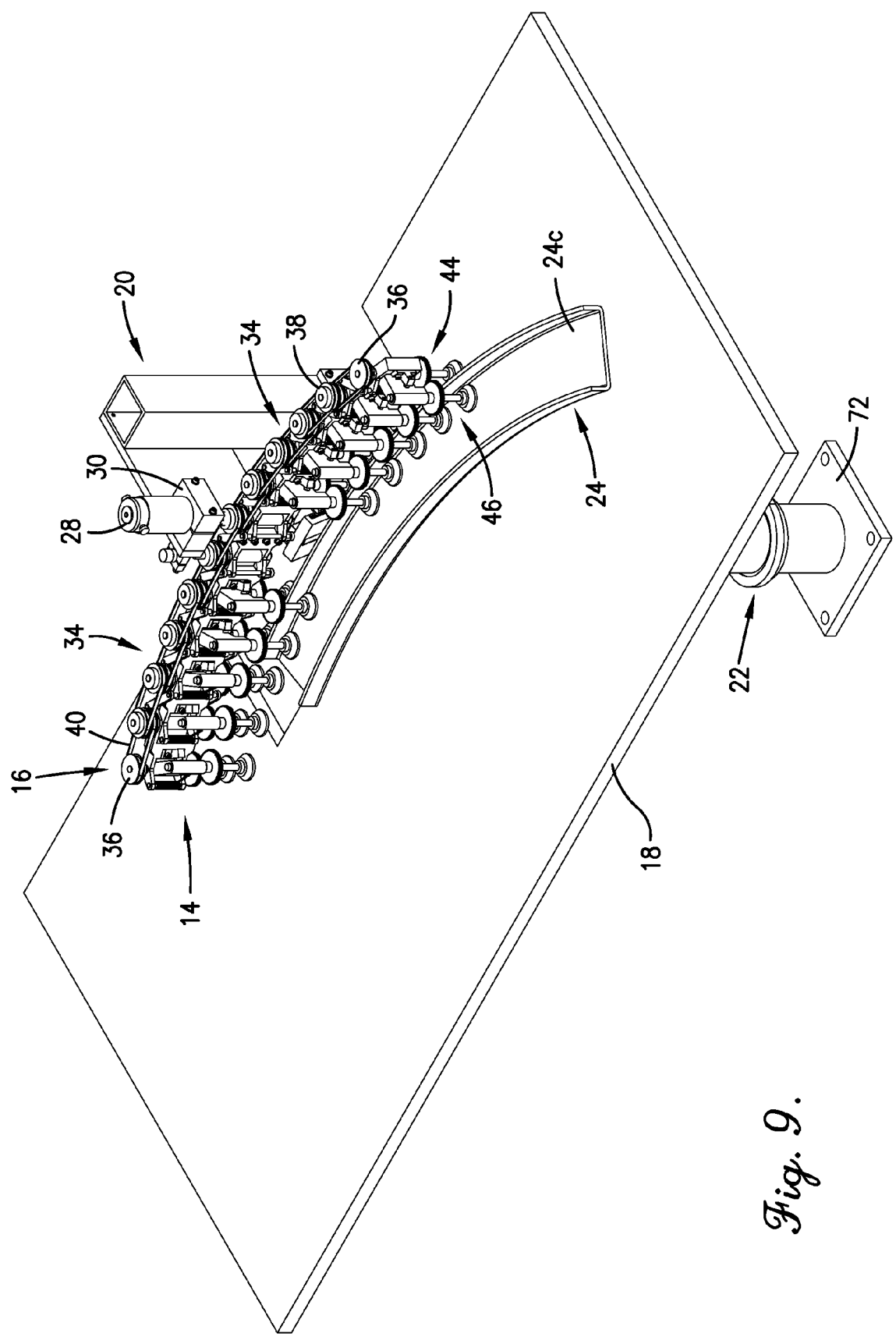
FIG. 9 is a perspective view of the apparatus scanning a curved test sample.
Figure 10:
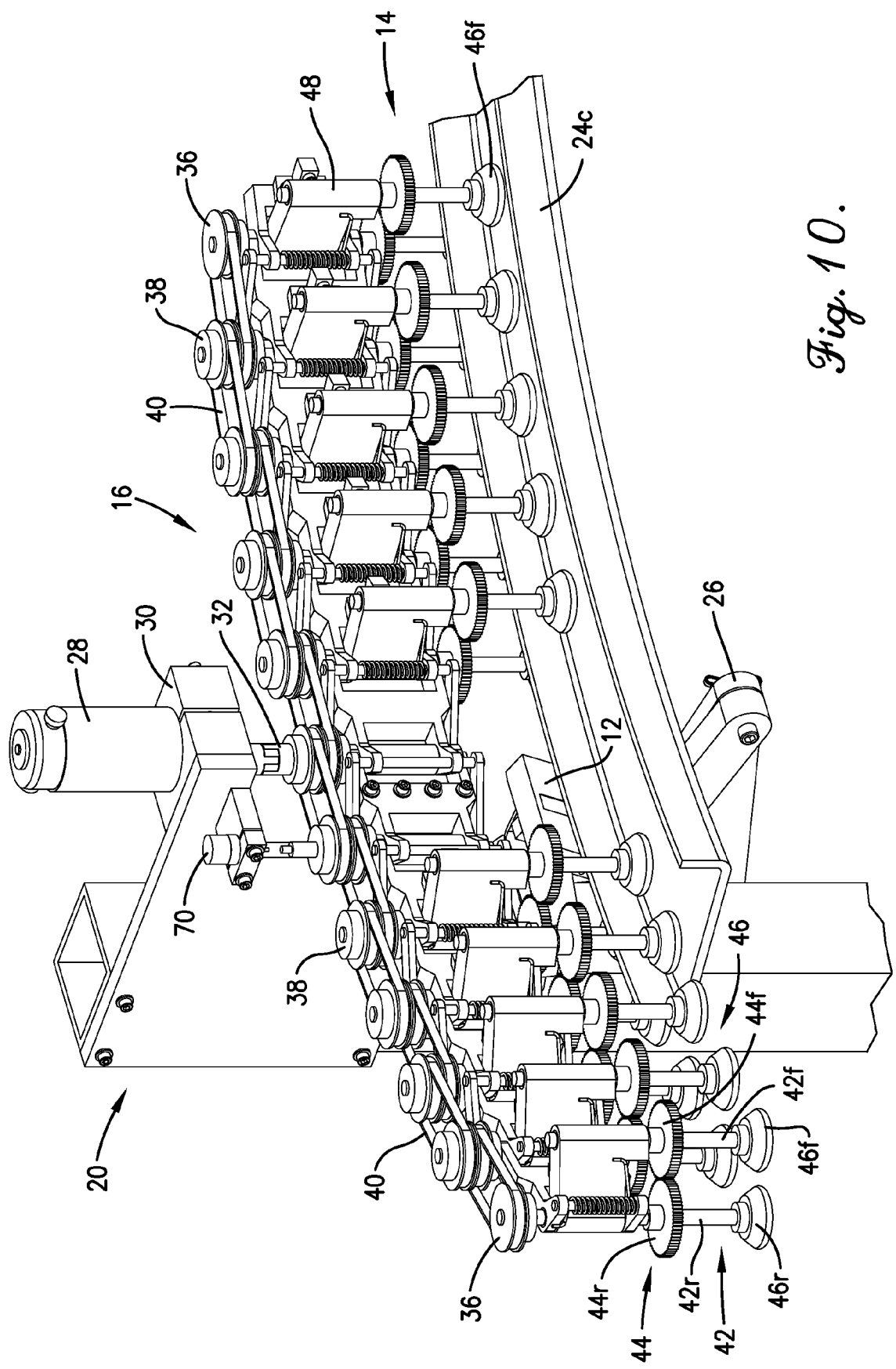
FIG. 10 is a perspective view of the apparatus scanning a curved test sample, showing greater detail.
Figure 11:
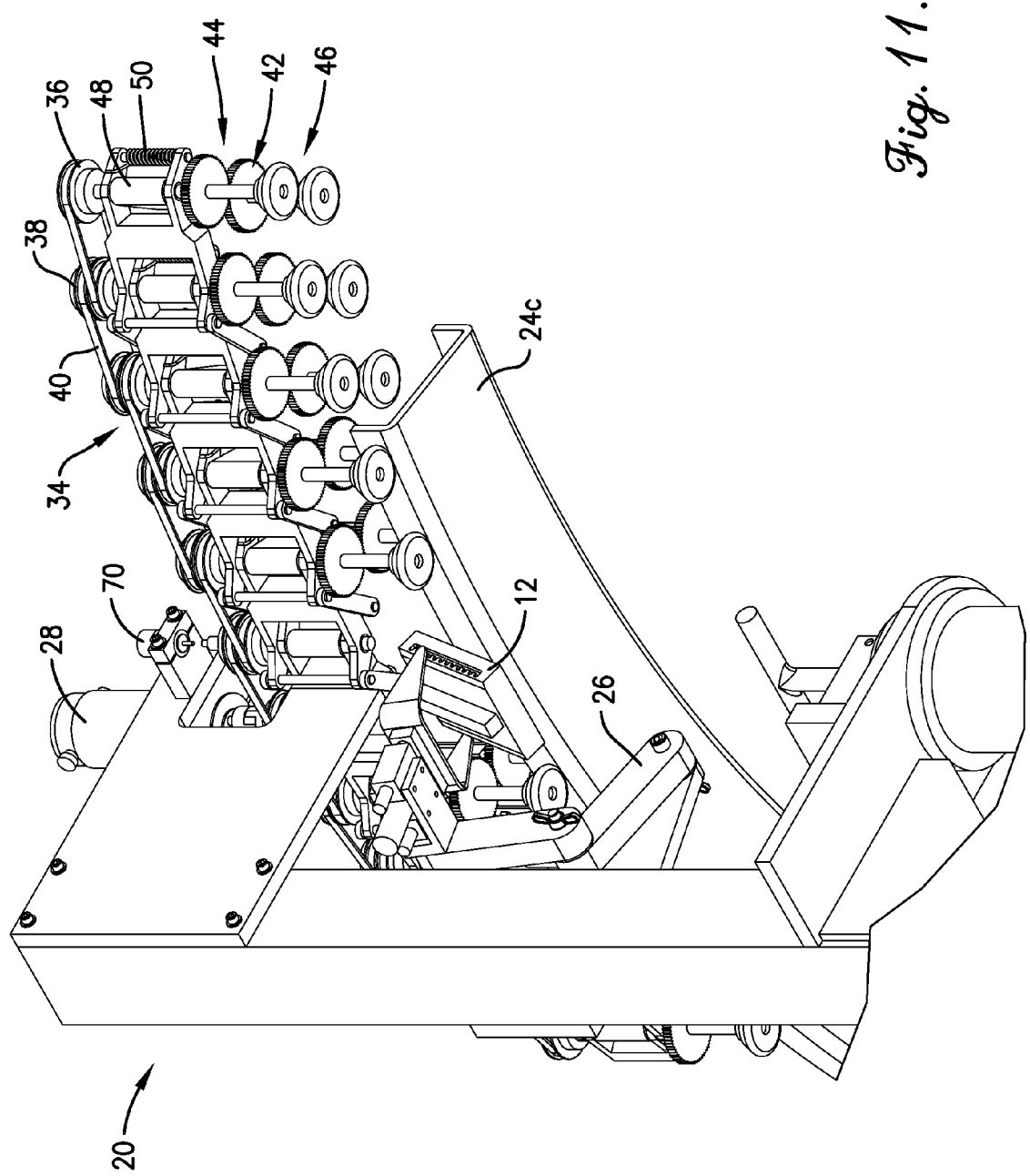
FIG. 11 is a perspective view of the apparatus scanning a curved test sample, as seen from underneath and slightly behind the apparatus.
Figure 12:
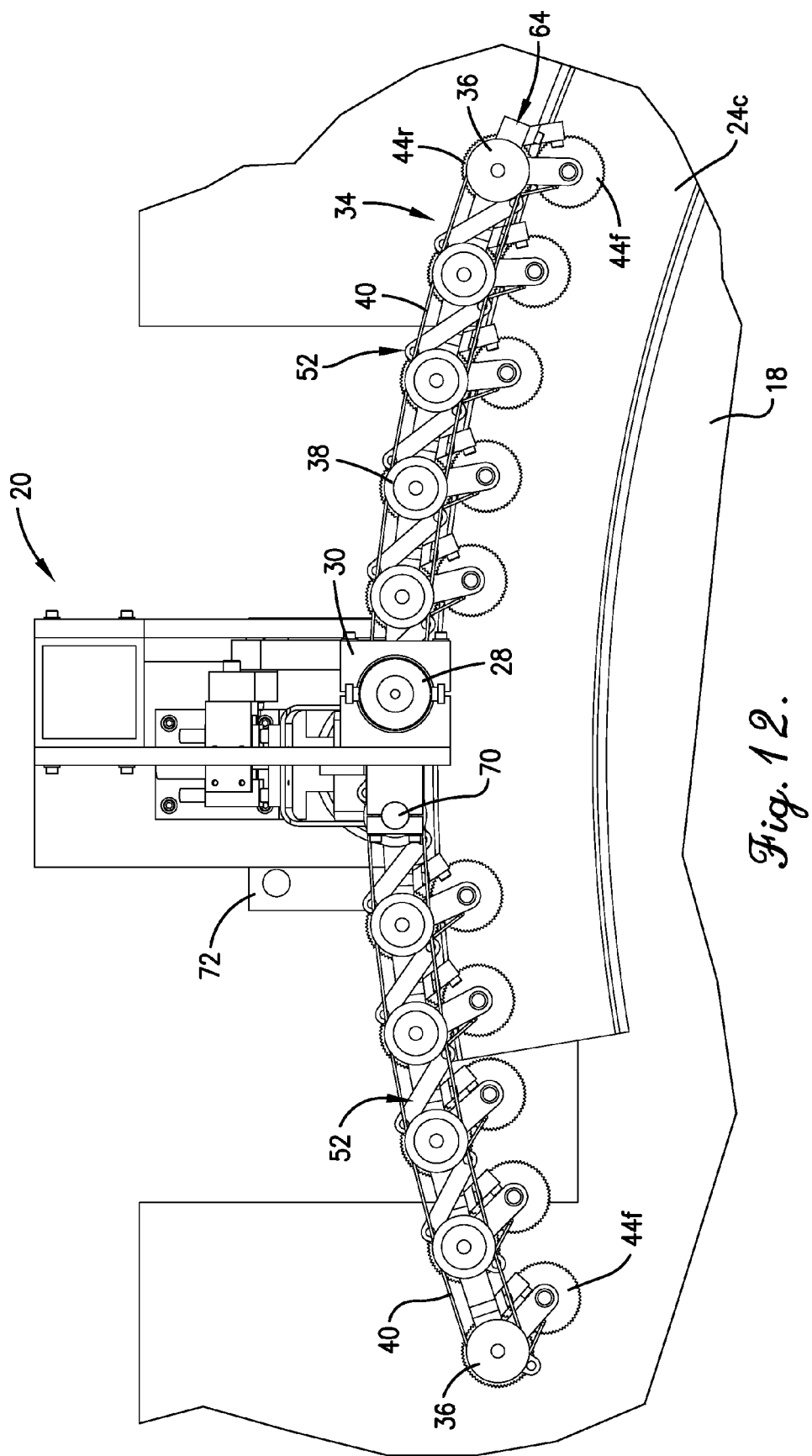
FIG. 12 is a top plan view of the apparatus scanning a curved test sample.

In various embodiments, the feed mechanism 14 also includes a plurality of shafts 42, gears 44, and rollers 46 that form two arrays—a rear array and a front array, best seen in FIG. 7 and FIG. 8. A front shaft 42$f$ is rigidly attached to a front gear 44$f$ and a front roller 46$f$. Likewise, a rear shaft 42$r$ is rigidly attached to a rear gear 44$r$ and a rear roller 46$r$. In addition, each rear shaft 42$r$ is rigidly coupled to a pulley 34 such that the rear shaft 42$r$, rear gear 44$r$, and rear roller 46$r$ rotate generally synchronously and in the same direction as the pulley 34.

The front shaft 42$f$ is loosely coupled to a swing arm 48 such that the front shaft 42$f$ may rotate within the swing arm 48. The swing arm 48 is also loosely coupled to the rear shaft 42$r$ such that the swing arm 48 may rotate or swing about the rear shaft 42$r$. Since a swing arm 48 connects each of the front shafts 42$f$ to a rear shaft 42$r$, the array of front components (shafts 42, gears 44, and rollers 46) forms in pairs with the array of rear components. For example, a pair of rollers 46 refers to the front roller 46$f$ and the rear roller 46$r$ that are attached to shafts 42 which are coupled through a swing arm 48.

The front gear 44$f$ aligns with and contacts the rear gear 44$r$ such that the teeth of the two gears mesh. The pair of gears 44$f$, 44$r$ are generally the same size and their teeth have the same pitch. As a result, the rotation of the rear gear 44$r$ causes an equal and opposite direction rotation of the front gear 44$f$. Since the rear gear 44$r$ is coupled to the rear roller 46$r$ through the rear shaft 42$r$ and the front gear 44$f$ is coupled to the front roller 46$f$ through the front shaft 42$f$, rotation of the rear roller 46$r$ causes an equal and opposite direction rotation of the front roller 46$f$.

In various embodiments, the structure of the feed mechanism 14 establishes its fundamental operation. The array of rear rollers 46$r$ are attached to the rear shafts 42$r$ that are connected to the pulleys 34 which are directly coupled through belts 40 to the drive shaft 32 of the drive motor 28. The front rollers 46$f$ are attached to the front shafts 42$f$ which are coupled to the rear shafts 42$r$ through the front and rear gears 44$f$, 44$r$. Thus, rotation of the drive motor 28 causes rotation of the array of rear rollers 46$r$ generally synchronously and in the same direction, while the array of front rollers 46$f$ rotates generally synchronously and in the opposite direction. Equal and opposite rotation of each pair of rollers 46$f$, 46$r$ propels the test sample 24 through the feed mechanism 14.

Figure 6:
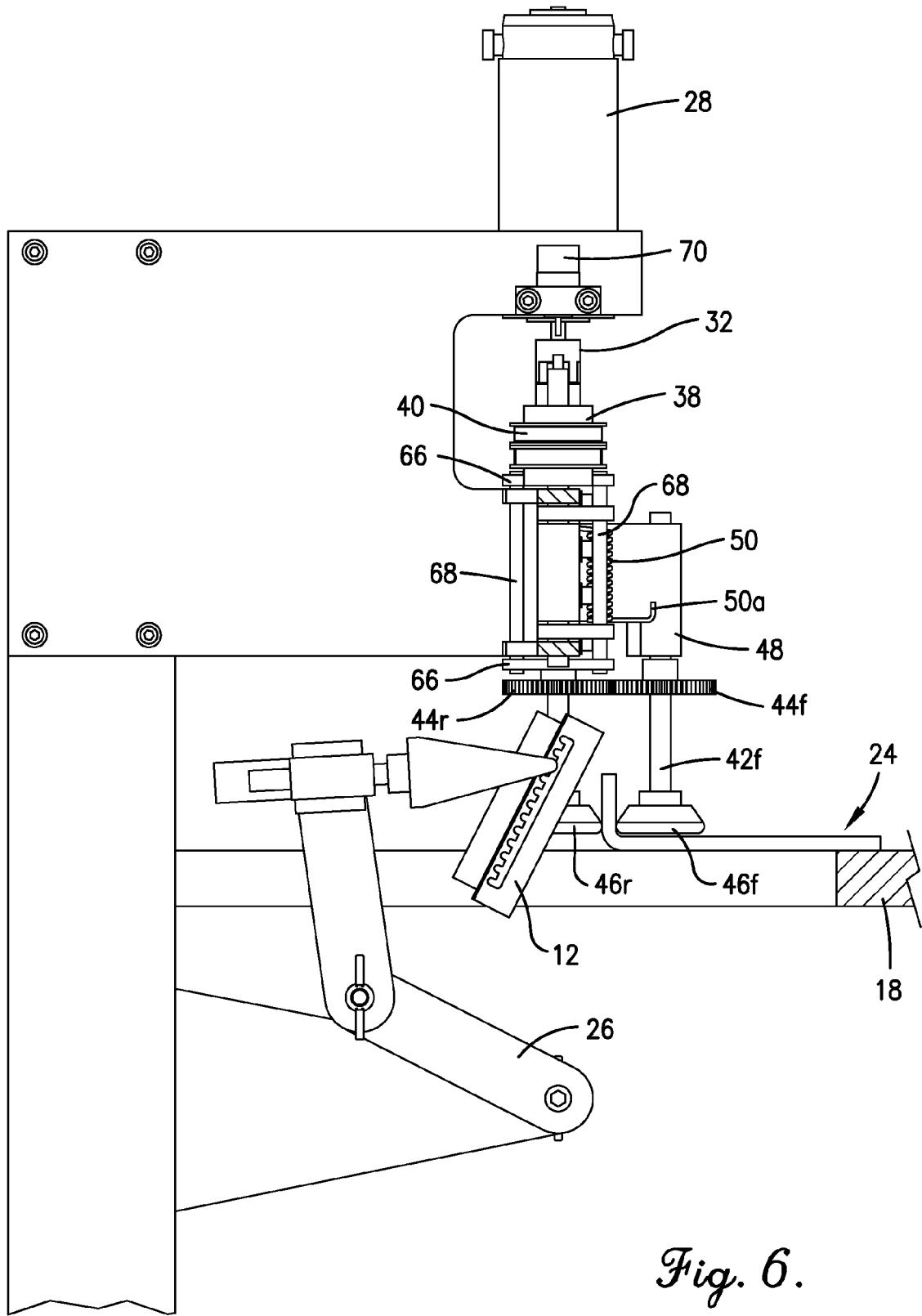
FIG. 6 is a side sectional view taken along line 6-6 in FIG. 5.

Structuring the rollers in pairs 46$f$, 46$r$ through the swing arms 48 allows the front roller 46$f$ to contact one side of the test sample 24 while the rear roller 46$r$ contacts the opposite side of the test sample 24, as seen in FIG. 6. In order to ensure the rollers 46$f$, 46$r$ can properly grip the test sample 24, the feed mechanism includes a spring element 50 that is attached to a secondary link 52 of the pivot mechanism 16. The spring element 50 includes a spring stub 50$a$ that applies pressure to the swing arm 48 to force the swing arm 48 to rotate about the rear shaft 42$r$. Thus, the front roller 46$f$ rotates about the rear roller 46$r$ in a counter-clockwise direction when viewed from above. The effect of the rotation is to squeeze the rollers 46$f$, 46$r$ onto the test sample 24 to hold the sample 24 steady as it is guided through the feed mechanism 14. To limit the rotation when a test sample 24 is not present, the feed mechanism 14 includes a stopper 54, which is mounted to a primary link 56 of the pivot mechanism 16. If the swing arm 48 and, by extension, the front roller 46$f$ overrotate, it is possible that the front roller 46$f$ could block the path of the test sample 24 through the feed mechanism 14.

In various embodiments, the pivot mechanism 16 adapts the feed mechanism 14 to the curvature of the test sample 24 in order to maintain a constant distance between the scanning element 12 and the sample 24. The pivot mechanism 16 comprises a plurality of primary links 56 and secondary links 52. The primary link 56 is elongated with a central body 58 that includes a pair of arms 60 and a pair of legs 62. The primary link 56 also includes a plurality of holes 56$a$, 56$b$, 56$c$, 56$d$. One of the primary links 56 is different from the others. The link 56 that is located at the entry point of the feed mechanism 14 (which is at the far right end when facing the scanning element 12) is a half-sized link 64 that does not include the legs 62 and holes 56$b$, 56$d$.

The primary link 56 is shaped in order to couple to other primary links 56 to form an open-ended chain. The arms 60 of one primary link 56 are adapted to fit within the interior portion of the legs 62 of another primary link 56. Holes 56$a$ on the arms 60 of one primary link 56 line up with holes 56$b$ on the legs 62 of another primary link 56 and a rear shaft 42 is inserted through the aligned holes 56$a$, 56$b$ to hold the links 56 together. Thus, the primary link 56 chain is formed, in various embodiments, with eleven full-sized links 56 and one half-sized link 64 coupled together.

The primary link 56 chain is attached to the frame 20 by a plurality of bolts at the sixth primary link 56 from the left side of the feed mechanism 14 when facing the scanning element 12 as shown in FIG. 6. Other forms of attachment are possible, however, the attachment must be strong enough to support the weight of the feed mechanism 14 and the pivot mechanism 16.

Each primary link 56 is operable to pivot about the rear shafts 42r at the points created by holes 56a, 56b. Thus, without consideration of the secondary links 52, the primary link 56 chain is like an average chain wherein each link 56 is free to pivot independently of the other links 56. However, haphazard and random pivoting of the primary links 56 is not desirable. To prevent uncoordinated pivoting of the primary links 56, the pivot mechanism 16 includes a plurality of secondary links 52.

In various embodiments, the secondary link 52 includes a pair of plates 66 and a pair of secondary shafts 68. The arms 60 of the primary link 56 bend at the elbows toward the front of the primary link 56 to include holes 56c and the legs 62 bend at the knees toward the rear of the primary link 56 to include holes 56d. The secondary shafts 68 are inserted into holes 56c, 56d in order to couple the legs 62 of one primary link 56 to the arms 60 of the link 56 that is two links away. Coupling every other primary link 56 together forces all of the links 56 to pivot whenever any one of the links 56 pivots. Thus, the primary links 56 pivot essentially in unison. As a result, when the primary links 56 pivot away from a straight-line formation, the links 56 form a generally smooth arc. In addition, since the rear rollers 46r are coupled to the primary links 56 through the rear shafts 42r and the front rollers 46f are coupled to the primary links 56 through the front shafts 42f and the swing arms 48, the feed mechanism 14 including the front and rear rollers 42f, 42r forms a generally smooth arc as well whenever the pivot mechanism 16 pivots. Therefore, the front and rear rollers 46f, 46r can adapt to the arc shape of a curved test sample 24c, as depicted in FIG. 9-FIG. 12. However, while the pivot mechanism 16 does adapt the feed mechanism 14 to the shape of the sample 24, the pivot mechanism 16 does not remain rigidly inflexible. The pivot mechanism 16 is flexible so that over the length of the test sample 14 minor variations in the curvature are permissible.

Furthermore, the feed mechanism 14 is operable to tolerate discontinuities in the test sample 24 along the edge where the rollers 46f, 46r grip the sample 24. The initial continuous portion in the test sample 24 must be at least the distance between three pairs of rollers 46 in length in order for the pivot mechanism 16 to establish the proper radius of curvature of the sample 24. Once the pivot mechanism 16 has adapted to the shape of the sample 24, then rollers 46f, 46r ahead of the discontinuity will continue to pull the test sample 24 forward while rollers 46 behind the discontinuity will continue to push the sample 24 forward so as to maintain uninterrupted forward motion of the sample 24 through the feed mechanism 14.

In various embodiments, the apparatus 10 also includes an encoder 70 to monitor the progress of the test sample 24 as the sample 24 moves through the feed mechanism 14. The encoder 70 may be attached to the frame 20 and positioned over one of the pulleys 34, as best seen in FIG. 2. The encoder 70 may monitor the position of the test sample 24 by tracking the number of revolutions of the local pulley 34. The encoder 70 may acquire this information through optical communication or through mechanical connection and then may feed the data to an external computer or test equipment.

The apparatus 10 may also include a base 22 with a pedestal 72. In various embodiments, the frame 20 as well as the rest of the apparatus 10 may revolve around the base 22 and the pedestal 72. The ability of the apparatus 10 to revolve around a fixed point may facilitate the feeding and unloading processes when testing curved samples.

Figure 13:
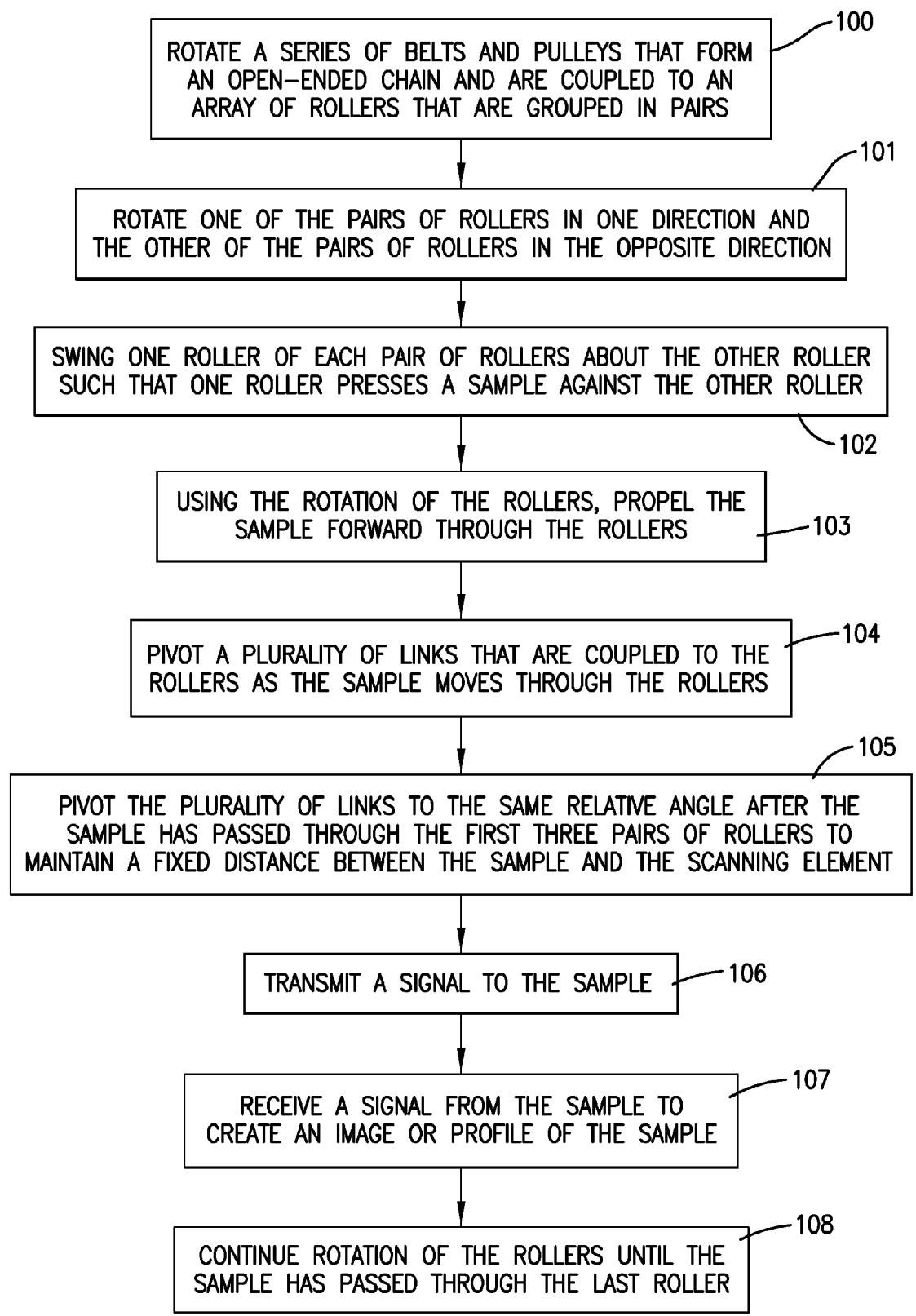
FIG. 13 is a flow diagram of steps performed by the apparatus.

The operation of the apparatus 10 is illustrated in FIG. 13. Activation of the drive motor 28 initiates rotation of the drive shaft 32 which in turn rotates the open-ended chain of pulleys 34 and belts 40 generally synchronously and in the same direction. Since each rear roller 46r is rigidly connected to a rear shaft 42r and each rear shaft 42r is rigidly connected to a pulley 34, the rear shafts 42r and the rear pulleys 46r rotate generally synchronously and in the same direction as the pulleys 34. The rear gears 44r are rigidly attached to the rear shafts 42r and couple with the front gears 44f. The front rollers 46r are rigidly attached to the front shafts 42f which are rigidly attached to the front gears 44f. As a result of coupling of the gears 44f, 44r, rotation of the rear shafts 42r results in rotation of the front shafts 42f in the opposite direction. Thus, activation of the drive motor 28 initiates rotation of the array of rear rollers 46r in one direction and rotation of the array of front rollers 46f generally synchronously with the rear rollers 46r and in the opposite direction, as listed in steps 100 and 101 of FIG. 13.

A test sample 24 is introduced to the entry point of the feed mechanism 14. The spring elements 50 exert a force on the swing arms 48 to rotate about the rear shafts 42r and rear rollers 46r. Due to the connection of the front shafts 42f (and by extension, front rollers 46f) to the swing arms 48, the force of the spring element 50 causes the front roller 46f of each pair of rollers 46 to rotate about the rear roller 46r, thus causing the front rollers 46f to squeeze against one side of the test sample 24 and the rear rollers 46r to squeeze against the other side of the test sample 24. Opposing rotation of the rollers 46f, 46r and pressure against the sides of the test sample 24 propels the sample 24 forward to the next pair of rollers 46, as listed in steps 102 and 103. A discontinuity, or gap, may exist in the test sample 24 along the edge where the rollers 46f, 46r grip the sample 24. Rollers 46f, 46r ahead of the discontinuity will continue to pull the test sample 24 forward while rollers 46 behind the discontinuity will continue to push the sample 24 forward so as to maintain uninterrupted forward motion of the sample 24 through the feed mechanism 14.

As the sample 24 moves forward through the feed mechanism 14, the encoder 70 tracks its progress. The primary links 56 pivot in unison to adapt to the curvature (if any) of the test sample. Given that three points define the circumference of a circle, once the test sample 24 passes through the third pair of rollers 46, the curvature of the pivot mechanism 16 is set and matches the curvature of the sample 24. The pivoting action of the pivot mechanism 16 ensures that the distance between the test sample 24 and the scanning element 12 is constant even when the radius of curvature of the test sample 24 varies from sample to sample, as listed in steps 104 and 105.

As the sample 24 continues through the feed mechanism 14 and passes in front of the scanning element 12, the scanning element 12 transmits a signal to the sample 24 and reads the signal back in order to create an image or profile of the sample 24 as it passes by, as listed in steps 106 and 107. The scanning element 12 scans the entire sample 24 and stores the scanned data for either real-time or post-scan analysis. The data may be transmitted to an external computer or test equipment.

As listed in step 108, after scanning the sample 24, the feed mechanism 14 continues to propel the sample forward until it has passed through the final pair of rollers 34.

Although the invention has been described with reference to the preferred embodiment illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A non-destructive inspection apparatus for inspecting samples that may include a curvature that varies from sample to sample, the apparatus comprising:
   a scanning element, operable to transmit a signal to a sample and receive a signal from the sample;
   a feed mechanism, operable to guide the sample past the scanning element, the feed mechanism including:
      a plurality of pulleys and a plurality of belts that form an open-ended chain, wherein each belt provides a link between two pulleys,
      a drive motor, coupled to the plurality of pulleys and the plurality of belts such that the drive motor can drive the series of pulleys to rotate generally synchronously and in the same direction,
      an array of rear elements including an array of rear shafts, an array of rear gears, and an array of rear rollers, wherein each rear element includes a rear shall rigidly attached to a rear gear and a rear roller, and
      an array of front elements including an array of front shafts, an array of front gears, and an array of front rollers, wherein each front element includes a front shaft rigidly attached to a front gear and a front roller, such that the array of rear gears contacts the array of front gears such that rotation of the array of rear elements in one direction causes rotation of the array of front elements in the opposite direction; and
   a pivot mechanism, operable to adapt the feed mechanism to the curvature of the sample in order to maintain a constant distance between the scanning element and the sample, the pivot mechanism including a plurality of primary links operable to pivot in response to the shape of the sample.

2. The apparatus of claim 1, further comprising an encoder in communication with the feed mechanism, operable to monitor the position of the sample as the sample is propelled past the scanning element.

3. The apparatus of claim 1, further comprising a frame, which supports the scanning element, the feed mechanism, and the pivot mechanism.

4. The apparatus of claim 1, wherein each one the of primary links includes a head and a tail such that the head of one primary link couples with the tail of the next primary link and each one the of primary links is operable to pivot about a point where the primary link is coupled to another primary link, and each one of the primary links is further coupled to one of the shafts of the rear array of elements at the point where one primary link is coupled to another primary link, such that as the primary links pivot, components of the feed mechanism move in relation to one another.

5. The apparatus of claim 4, wherein a plurality of secondary links couple the tail of one primary link to the head of the primary link that is two links away, to provide global connection of the pivot mechanism so that when one of the primary links pivots, all of the primary links pivot generally in unison to form an arc, thereby adapting the feed mechanism to the curvature of the sample.

6. The apparatus of claim 1, wherein the feed mechanism further includes a plurality of swing arms that couples the array of rear shafts to the array of front shafts such that the array of rear elements is generally aligned with the array of front elements to form pairs of elements including pairs of gears, pairs of shafts, and pairs of rollers, and such that the array of front elements can swing about the array of rear elements.

7. The apparatus of claim 6, wherein the array of rear shafts is coupled to the plurality of pulleys such that the drive motor is operable to drive the plurality of pulleys and the array of rear elements to rotate generally synchronously and in one direction and the array of front elements to rotate generally synchronously and in the opposite direction.

8. The apparatus of claim 7, wherein the rear roller of each pair of rollers contacts one side of the sample and the front roller of each pair of rollers contacts the other side of the sample and the feed mechanism further includes a plurality of springs that apply pressure to the swing arms to force the front rollers to swing about the rear rollers, thereby allowing the front rollers to press the sample against the rear rollers.

9. The apparatus of claim 8, wherein the feed mechanism further includes a plurality of stoppers that limit the swing angle of the array of front rollers about the array of rear rollers in order to allow the sample to pass through each pair of rollers.

10. A non-destructive inspection apparatus for inspecting samples that may include a curvature that varies from sample to sample, the apparatus comprising:
    a scanning element, operable to transmit a signal to a sample and receive a signal from the sample;
    a feed mechanism, operable to guide the sample past the scanning element, the feed mechanism including:
       a plurality of pulleys and a plurality of belts that form an open-ended chain, wherein each belt provides a link between two pulleys,
       a drive motor, coupled to the plurality of pulleys and the plurality of belts such that the drive motor can drive the series of pulleys to rotate generally synchronously and in the same direction,
       an array of rear elements including an array of rear shafts, an array of rear gears, and an array of rear rollers, wherein each rear element includes a rear shaft rigidly attached to a rear gear and a rear roller; and
    a pivot mechanism, operable to adapt the feed mechanism to the curvature of the sample in order to maintain a constant distance between the scanning element and the sample, the pivot mechanism including:
       a plurality of primary links operable to pivot in response to the shape of the sample,
       wherein each one the of primary links includes a head and a tail such that the head of one primary link couples with the tail of the next primary link and each one the of primary links is operable to pivot about a point where the primary link is coupled to another primary link, and each one of the primary links is further coupled to one of the shafts of the rear array of elements at the point where one primary link is coupled to another primary link, such that as the primary links pivot, components of the feed mechanism move in relation to one another, and
       wherein a plurality of secondary links couple the tail of one primary link to the head of the primary link that is two links away, to provide global connection of the pivot mechanism so that when one of the primary links pivots, all of the primary links pivot generally in unison to form an arc, thereby adapting the feed mechanism to the curvature of the sample.

11. The apparatus of claim 10, further comprising an encoder in communication with the feed mechanism, operable to monitor the position of the sample as the sample is propelled past the scanning element.

12. The apparatus of claim 10, further comprising a frame, which supports the scanning element, the feed mechanism, and the pivot mechanism.

13. The apparatus of claim 10, wherein the feed mechanism further includes an array of front elements including an array of front shafts, an array of front gears, and an array of front rollers, wherein each front element includes a front shaft rigidly attached to a front gear and a front roller, such that the array of rear gears contacts the array of front gears such that rotation of the array of rear elements in one direction causes rotation of the array of front elements in the opposite direction.

14. The apparatus of claim 10, wherein the feed mechanism further includes a plurality of swing arms that couples the array of rear shafts to the array of front shafts such that the array of rear elements is generally aligned with the array of front elements to form pairs of elements including pairs of gears, pairs of shafts, and pairs of rollers, and such that the array of front elements can swing about the array of rear elements.

15. The apparatus of claim 14, wherein the array of rear shafts is coupled to the plurality of pulleys such that the drive motor is operable to drive the plurality of pulleys and the array of rear elements to rotate generally synchronously and in one direction and the array of front elements to rotate generally synchronously and in the opposite direction.

16. The apparatus of claim 15, wherein the rear roller of each pair of rollers contacts one side of the sample and the front roller of each pair of rollers contacts the other side of the sample and the feed mechanism further includes a plurality of springs that apply pressure to the swing arms to force the front rollers to swing about the rear rollers, thereby allowing the front rollers to press the sample against the rear rollers.

17. The apparatus of claim 16, wherein the feed mechanism further includes a plurality of stoppers that limit the swing angle of the array of front rollers about the array of rear rollers in order to allow the sample to pass through each pair of rollers.

* * * * *